(12) United States Patent
Takihi

(10) Patent No.: US 8,338,789 B2
(45) Date of Patent: Dec. 25, 2012

(54) RADIATION DETECTOR

(75) Inventor: Shinji Takihi, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 315 days.

(21) Appl. No.: 12/672,212

(22) PCT Filed: Sep. 24, 2008

(86) PCT No.: PCT/JP2008/067193
§ 371 (c)(1),
(2), (4) Date: Feb. 4, 2010

(87) PCT Pub. No.: WO2009/044657
PCT Pub. Date: Apr. 9, 2009

(65) Prior Publication Data
US 2011/0095191 A1    Apr. 28, 2011

(30) Foreign Application Priority Data
Oct. 1, 2007    (JP) ................. P2007-257960

(51) Int. Cl.
*G01T 1/20*    (2006.01)
(52) U.S. Cl. ....................................... 250/366
(58) Field of Classification Search .......... 250/366, 250/370.08, 370.09, 370.11, 370.12
See application file for complete search history.

(56) References Cited

U.S. PATENT DOCUMENTS
2002/0070365 A1 * 6/2002 Karellas ............... 250/581

FOREIGN PATENT DOCUMENTS

| JP | 5-68674 | 9/1985 |
|---|---|---|
| JP | S60-200189 | 10/1985 |
| JP | 62-075368 | 4/1987 |
| JP | 1-129184 | 5/1989 |
| JP | 2-151789 | 6/1990 |
| JP | 5-25383 | 4/1993 |
| JP | H7-027865 | 1/1995 |
| JP | H7-084056 | 3/1995 |
| JP | H7-120557 | 5/1995 |
| JP | 10-010235 | 1/1998 |

(Continued)

*Primary Examiner* — David Porta
*Assistant Examiner* — Faye Boosalis
(74) *Attorney, Agent, or Firm* — Drinker Biddle & Reath LLP

(57) ABSTRACT

In an X-ray line sensor 1, a scintillator layer 24 that absorbs X-rays in a low-energy range and emits light and a scintillator layer 26 that absorbs X-rays in a high-energy range and emits light are brought in contact with each other, and further, the thickness of the scintillator layer 24 on the front side is thinner than that of the scintillator layer 26 on the rear side. These make the amount of mismatch small between a light emitting position P1 in the scintillator layer 24 and a light emitting position P2 in the scintillator layer 26 to X-rays in the low-energy range and X-rays in the high-energy range entered at the same angle from the front side, so that at this time, light emitted by the scintillator layer 24 and light emitted by the scintillator layer 26 are detected by a photo-detecting section 16 and a photo-detecting section 23 facing each other. Thus, mismatch between an X-ray transmission image in the low-energy range and an X-ray transmission image in the high-energy range obtained simultaneously can be prevented.

9 Claims, 4 Drawing Sheets

FOREIGN PATENT DOCUMENTS

| | | |
|---|---|---|
| JP | 10-093061 | 4/1998 |
| JP | 11-505142 | 5/1999 |
| JP | 2002-048872 | 2/2002 |
| JP | 2002-101265 | 4/2002 |
| JP | 2002-116261 | 4/2002 |
| JP | 2003-119070 | 4/2003 |
| JP | 2004-061492 | 2/2004 |
| JP | 2004-177217 | 6/2004 |
| JP | 2007-052024 | 3/2007 |
| WO | WO 96/35372 | 11/1996 |

* cited by examiner

RADIATION DETECTOR

TECHNICAL FIELD

The present invention relates to a dual-energy radiation detector.

BACKGROUND ART

A dual-energy radiation detector is an apparatus that detects radiation in a low-energy range and radiation in a high-energy range transmitted through a specimen (refer to, for example, Patent Document 1). According to such a radiation detector, by simultaneously obtaining a radiation image in the low-energy range and a radiation image in the high-energy range and preparing, based on those radiation images, a processed image applied with a predetermined processing (for example, a weighted subtraction, superimposition, or the like), detection of a foreign substance, measurement of the component distribution, measurement of the weight, and the like can be realized at high accuracy in a non-destructive inspection (that is, an in-line non-destructive inspection) of the specimen that is conveyed by a conveyor or the like.

Patent Document 1: Japanese Published Examined Patent Application No. H05-68674

DISCLOSURE OF THE INVENTION

Problem to be Solved by the Invention

However, a further improvement in reliability has been expected for the dual-energy radiation detector, such as preventing mismatch between a radiation image in the low-energy range and a radiation image in the high-energy range obtained simultaneously.

The present invention has therefore been made in view of such circumstances, and an object thereof is to provide a highly reliable radiation detector.

Means for Solving the Problem

In order to achieve the above-described object, a radiation detector according to the present invention, which is a radiation detector for detecting radiation in a first energy range and radiation in a second energy range entered from a front side, includes: a first scintillator layer extending along a predetermined direction, for converting radiation in the first energy range to light; a first photodetector having a plurality of first photo-detecting sections being disposed one-dimensionally along the predetermined direction and fixed to a front side of the first scintillator layer, for converting light converted by the first scintillator layer to an electrical signal, and a first substrate with the first photo-detecting sections provided; a second scintillator layer extending in the predetermined direction and being brought in contact with a rear side of the first scintillator layer, for converting radiation in the second energy range to light; and a second photodetector having a plurality of second photo-detecting sections being disposed one-dimensionally along the predetermined direction and fixed to a rear side of the second scintillator layer, for converting light converted by the second scintillator layer to an electrical signal, and a second substrate with the second photo-detecting sections provided, in which the first scintillator layer has a thickness thinner than that of the second scintillator layer, when viewed from a front side, in a direction perpendicular to the predetermined direction, one edge portion of the first substrate is located outside further than one edge portion of the second substrate, and the other edge portion of the second substrate is located outside further than the other edge portion of the first substrate.

In this radiation detector, the first scintillator layer that converts radiation in the first energy range to light and the second scintillator layer that converts radiation in the second energy range to light are brought in contact with each other, and further, the thickness of the first scintillator layer disposed on the front side is thinner than that of the second scintillator layer disposed on the rear side. These make the amount of mismatch small between a light emitting position in the first scintillator layer and a light emitting position in the second scintillator layer to radiation in the first energy range and radiation in the second energy range entered at the same angle from the front side. Thus, mismatch between a radiation image in the first energy range and a radiation image in the second-energy range obtained simultaneously can be prevented. Moreover, in this radiation detector, one edge portion of the first substrate with the first photo-detecting section provided is located outside further than one edge portion of the second substrate with the second photo-detecting section provided, and conversely, the other edge portion of the second substrate is located outside further than the other edge portion of the first substrate. Therefore, even when the first substrate and the second substrate approach each other as a result of reducing the thickness of the first scintillator layer, by disposing a circuit, a connector, and the like at a part not overlapping the second substrate in the first substrate and a part not overlapping the first substrate in the second substrate, irradiation of radiation onto the circuit, the connector, and the like can be avoided. As above, according to this radiation detector, it becomes possible to improve reliability.

Also, the radiation in the first energy range means radiation having a predetermined range of energy, while the radiation in the second energy range means radiation having a range of energy different from the predetermined range.

It is preferable that the radiation detector according to the present invention includes a slit structure being disposed on a front side of the first photodetector, for passing radiation in the first energy range and radiation in the second energy range, the slit structure has a first plate-like member formed with a slit extending in the predetermined direction, and a second plate-like member that supports the first plate-like member from a rear side, and in the second plate-like member, a wall portion provided in a standing condition toward the rear side is formed along one edge portion and the other edge portion of the slit. In this case, even when a relatively soft material such as lead is used for the first plate-like member so as to reliably shield radiation, deformation of the slit formed in the first plate-like member is prevented by the second plate-like member, so that radiation can be made incident reliably on a line along the predetermined direction.

It is preferable in the radiation detector according to the present invention that, when viewed from a front side, in a direction perpendicular to the predetermined direction, the first scintillator layer has a width wider than that of the slit. In this case, even when the thickness of the first scintillator layer is reduced, a decline in strength of the first scintillator layer can be suppressed, and radiation in the first energy range can be reliably converted to light by the first scintillator layer.

It is preferable in the radiation detector according to the present invention that the first photo-detecting sections, at least two of which being formed on each of a plurality of first photo-detecting devices disposed one-dimensionally along the predetermined direction with a first gap being secured therebetween, are thus disposed one-dimensionally along the predetermined direction, the first scintillator layer is disposed on a rear side of the first photo-detecting device and the first gap, the second photo-detecting sections, at least two of which being formed on each of a plurality of second photo-detecting devices disposed one-dimensionally along the predetermined direction with a second gap being secured therebetween, are thus disposed one-dimensionally along the predetermined direction, and the second scintillator layer is disposed on a front side of the second photo-detecting device. This allows the adjacent photo-detecting devices to avoid contact and damage with each other. Moreover, in the first photo-detecting section, the first scintillator layer is disposed not only on the rear side of the photo-detecting device but also on the rear side of the first gap. It is preferable that the first scintillator layer is formed integrally across the predetermined direction, and in this case, because the scintillator layer is disposed not only on the photo-detecting device but also on the gap between the adjacent photo-detecting devices, generation of a dead zone on a line along the predetermined direction can be prevented.

It is preferable in the radiation detector according to the present invention that the second scintillator layer has a plurality of scintillator portions disposed one-dimensionally along the predetermined direction, and a reflection layer that covers the scintillator portion excluding a part to which the second photo-detecting section is fixed, the scintillator portion absorbs radiation in the second energy range and emits light, and the reflection layer passes radiation in the second energy range, and also reflects light emitted by the first scintillator layer and light emitted by the scintillator portion, and is also formed so that parts facing each other in a direction perpendicular to the predetermined direction when viewed from a front side has a thickness thicker than that of the other part. In this case, generation of crosstalk between the adjacent second photo-detecting sections can be prevented. Further, even when the scintillator portion of the second scintillator layer is in a prism shape in order to maintain a high resolution while converting radiation in the high-energy range to light, because the reflection layer is formed so that the thickness of the parts facing each other in the direction perpendicular to the predetermined direction becomes thicker than that of the other part, the scintillator portion can be reliably supported.

Effects of the Invention

According to the present invention, it becomes possible to improve the reliability of the radiation detector.

DESCRIPTION OF REFERENCE NUMERALS

Figure 1:
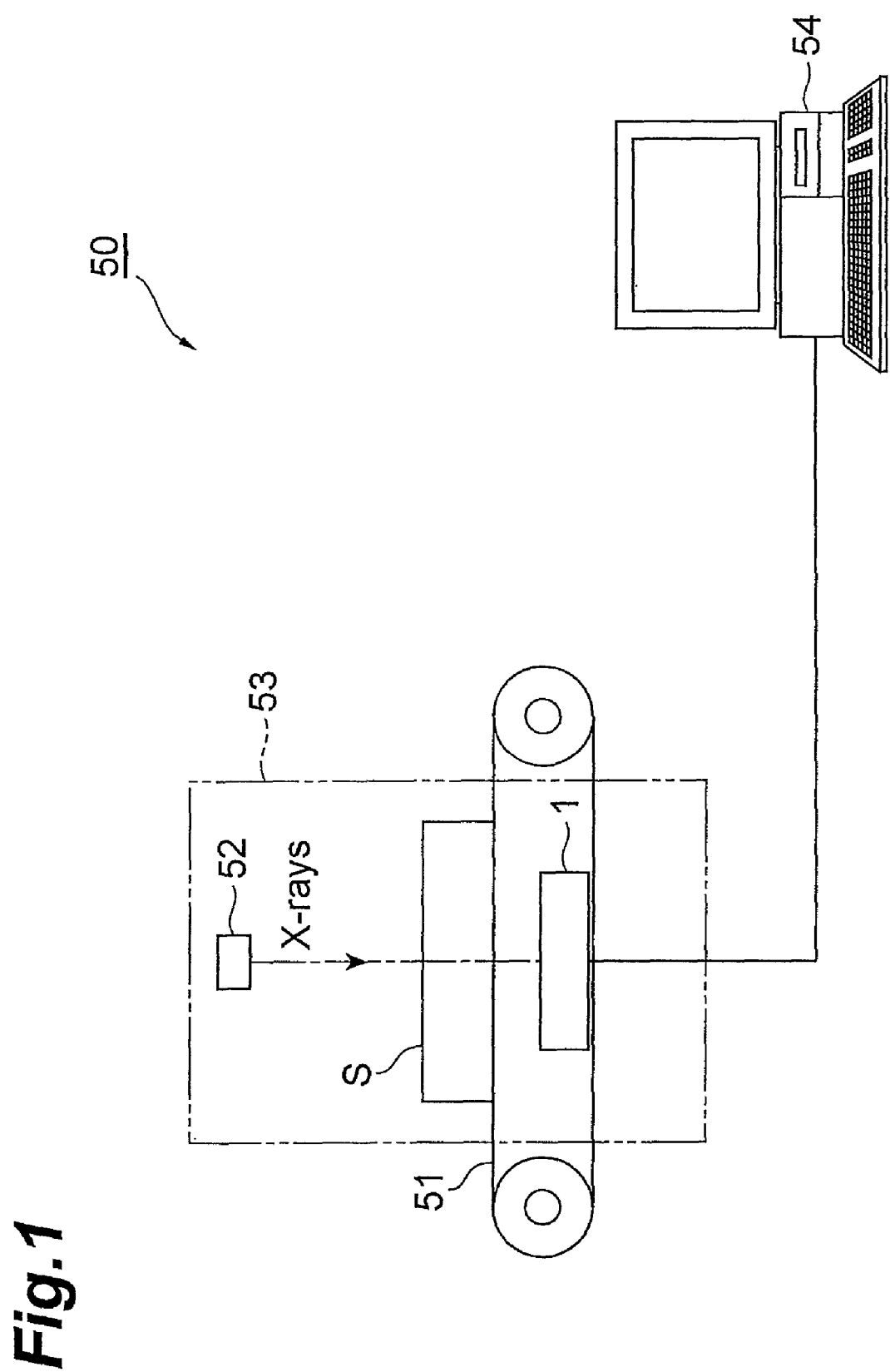
FIG. 1 is a configurational view of a non-destructive inspection system applied with an X-ray line sensor, which is an embodiment of a radiation detector according to the present invention.

1 . . . X-ray line sensor, 6 . . . slit structure, 7 . . . first plate-like member, 7*a* . . . slit, 8 . . . second plate-like member, 8*a* . . . wall portion, 11 . . . first photodetector, 12 . . . first substrate, 12*a* . . . one edge portion of first substrate, 12*b* . . . other edge portion of first substrate, 13 . . . first gap, 14 . . . first photo-detecting device, 16 . . . first photo-detecting section, 17 . . . second photodetector, 18 . . . second substrate, 18*a* . . . one edge portion of second substrate, 18*b* . . . other edge portion of second substrate, 19 . . . second gap, 21 . . . second photo-detecting device, 23 . . . second photo-detecting section, 24 . . . first scintillator layer, 26 . . . second scintillator layer, 28 . . . scintillator portion, 29 . . . reflection layer.

BEST MODES FOR CARRYING OUT THE INVENTION

Hereinafter, a preferred embodiment of the present invention will be described in detail with reference to the drawings. Also, the same or corresponding parts are denoted with the same reference numerals in the figures, and overlapping description will be omitted.

FIG. 1 is a configurational view of a non-destructive inspection system applied with an X-ray line sensor, which is an embodiment of a radiation detector according to the present invention. As shown in FIG. 1, a non-destructive inspection system 50 includes a belt conveyor 51 that conveys a specimen S, an X-ray source 52 that emits X-rays toward the specimen S being conveyed by the conveyor 51, a dual-energy X-line sensor (one-dimensional sensor) 1 that detects X-rays in a low-energy range (radiation in a first energy range) and X-rays in a high-energy range (radiation in a second energy range) transmitted through the specimen S, an X-ray shield box 53 that covers the specimen S, the X-ray source 52, and the X-line sensor 1, and a computer 54 electrically connected with the X-ray line sensor 1. The computer 54 prepares a processed image applied with a predetermined processing (for example, a weighted subtraction, superimposition, or the like) based on an X-ray transmission image in the low-energy range and an X-ray transmission image in the high-energy range obtained simultaneously.

Hereinafter, although a one-dimensional sensor will be exemplified by a line sensor, the present invention is by no means limited thereto, and examples of another one-dimensional sensor applicable to a radiation detector according to the present invention include a TDI sensor and the like.

According to the non-destructive inspection system 50 thus configured, for a specimen S such as food or electronic components, a measurement of the component distribution, a measurement of the weight, and the like besides detection of a foreign substance can be realized at high accuracy.

Figure 2:
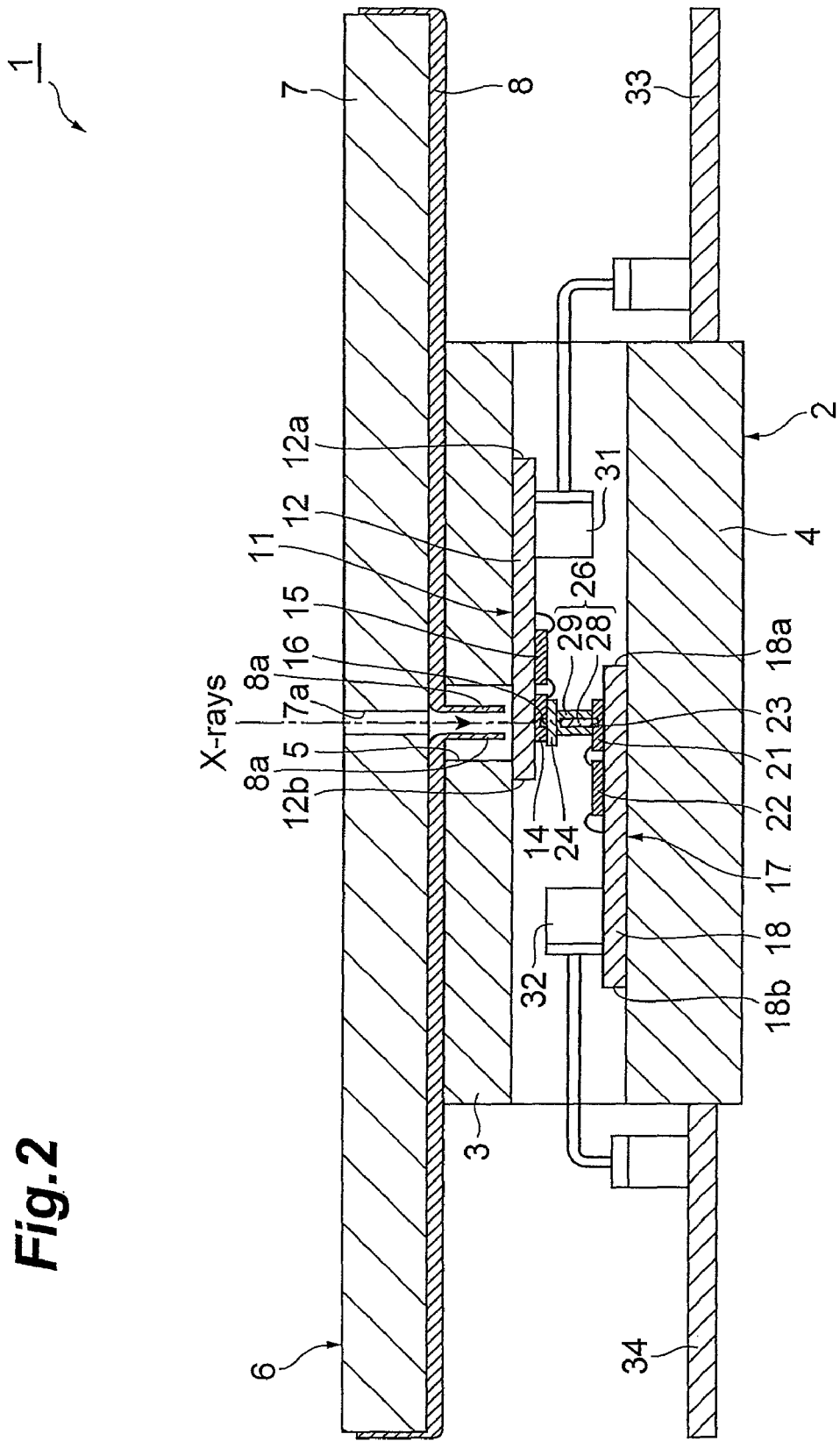
FIG. 2 is a sectional view of the X-ray line sensor of FIG. 1.
Figure 3:
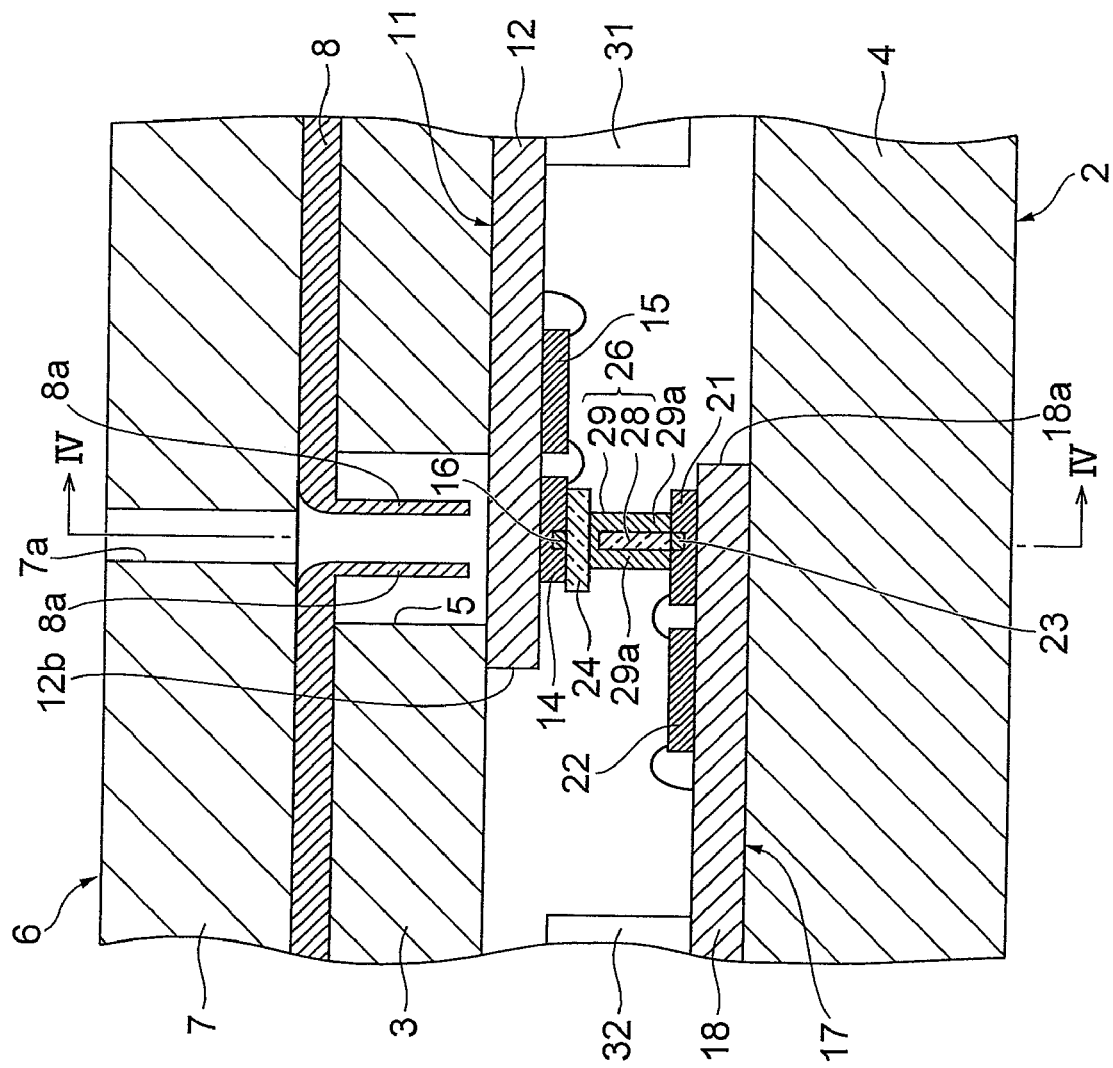
FIG. 3 is an enlarged view of a main part of the X-ray line sensor of FIG. 2.
Figure 4:
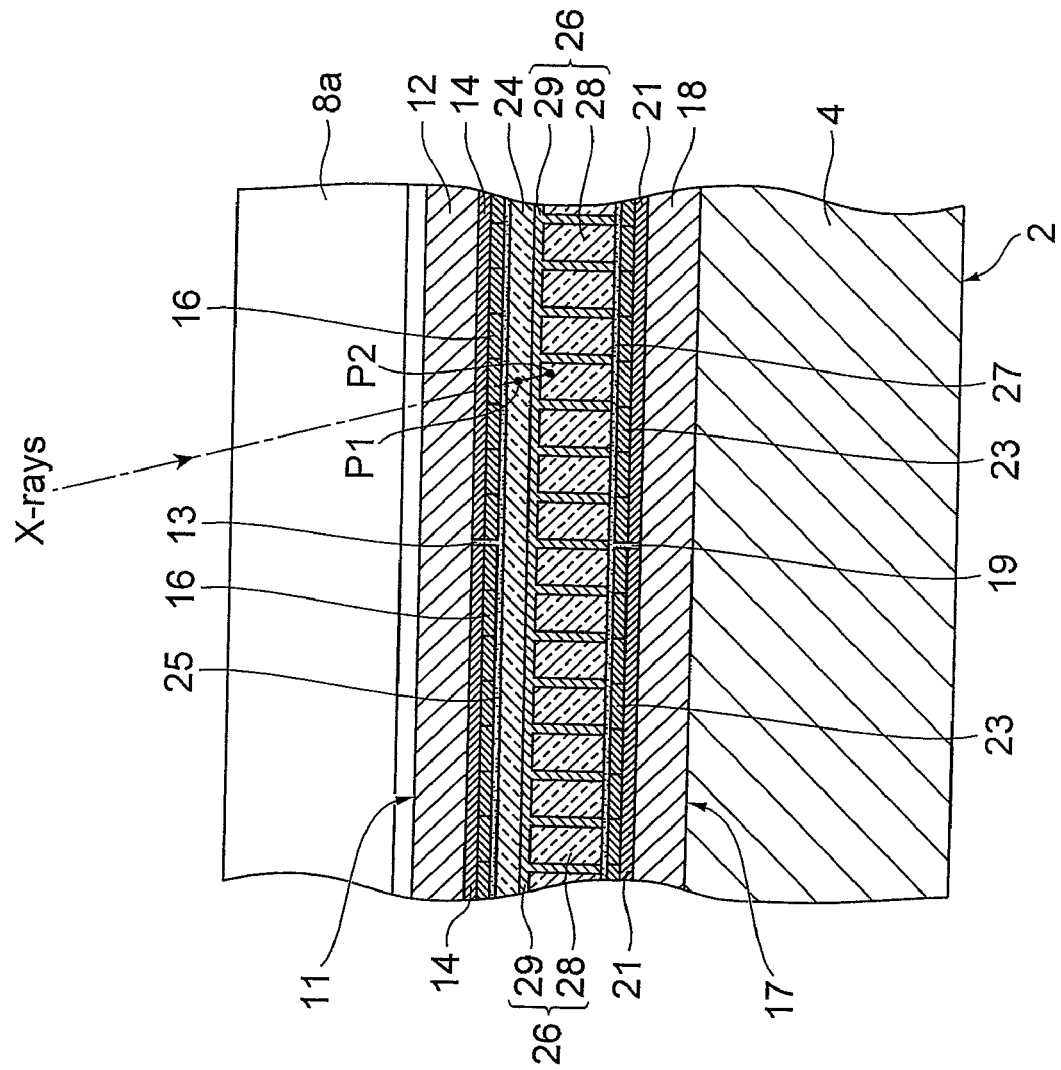
FIG. 4 is a sectional view taken along a line IV-IV of the X-ray line sensor of FIG. 3.

FIG. 2 is a sectional view of the X-ray line sensor of FIG. 1, FIG. 3 is an enlarged view of a main part of the X-ray line sensor of FIG. 2, and FIG. 4 is a sectional view taken along a line IV-IV of the X-ray line sensor of FIG. 3. As shown in FIGS. 2 to 4, the X-ray line sensor 1 includes a rectangular parallelepiped-shaped mechanism 2 made of aluminum. The mechanism 2 has a front step portion 3 that forms a front side (X-ray source 52 side) and a rear step portion 4 that forms a rear side, and an opening 5 is provided in the front step portion 3.

At the front side of the mechanism 2, a slit structure 6 to pass X-rays emitted from the X-ray source 52 is attached. The slit structure 6 has a first plate-like member 7 formed with a slit 7*a* extending in a predetermined direction (a direction perpendicular to a conveying direction of the specimen S when viewed from the front side) and a second plate-like member 8 that supports the first plate-like member 7 from the rear side. The first plate-like member 7 is made of a metal (for example, lead) that shields X-rays, and the second plate-like member 8 is made of a metal (for example, stainless steel) of a higher hardness than that of the metal used for the first plate-like member 7.

In the second plate-like member 8, a wall portion 8a provided in a standing condition toward the rear side is formed along one edge portion and the other edge portion extending in a longitudinal direction of the slit 7a. The wall portion 8a is disposed within the opening 5 provided in the front step portion 3 of the mechanism 2.

At an inner surface of the front step portion 3 of the mechanism 2, a first photodetector 11 is attached. The first photodetector 11 has a rectangular plate-shaped first substrate 12 fixed to the front step portion 3 of the mechanism 2, a plurality of (for example, 8 to 14) first photo-detecting devices 14 disposed one-dimensionally on the first substrate 12 along the predetermined direction with a slight first gap 13 being secured therebetween, and an amplifier circuit 15 or the like disposed on the first substrate 12 and electrically connected with each photo-detecting device 14 by wire bonding. In the first photo-detecting device 14, a first photo-detecting section 16 being a photoelectric transducer is formed in plurality (for example, 128) one-dimensionally along the predetermined direction, so as to face the slit 7a in an incident direction of X-rays (a direction perpendicular to the conveying direction of the specimen S and the predetermined direction).

At an inner surface of the rear step portion 4 of the mechanism 2, a second photodetector 17 is attached. The second photodetector 17 has a rectangular plate-shaped second substrate 18 fixed to the rear step portion 4 of the mechanism 2, a plurality of (for example, 8 to 14) second photo-detecting devices 19 disposed one-dimensionally on the second substrate 18 along the predetermined direction with a slight second gap 19 being secured therebetween, and an amplifier circuit 22 or the like disposed on the second substrate 18 and electrically connected with each photo-detecting device 21 by wire bonding. In the second photo-detecting device 21, a second photo-detecting section 23 being a photoelectric transducer is formed in plurality (for example, 128) one-dimensionally along the predetermined direction, so as to face each of the first photo-detecting sections 16 in the incident direction of X-rays.

Also, the configuration of the first photodetector 11 is substantially identical to that of the second photodetector 17, and as the photo-detecting devices 14, 21, line sensors such as, for example, CCDs, or CMOSs are used. In addition, when viewed from the front side, in the direction perpendicular to the predetermined direction, one edge portion 12a of the first substrate 12 is located outside further than one edge portion 18a of the second substrate 18, and the other edge portion 18b of the second substrate 18 is located outside further than the other edge portion 12b of the first substrate 12.

On the rear side of the first photo-detecting device 14 and the first gap 13, disposed is a first scintillator layer 24 that extends along the predetermined direction, and absorbs X-rays in the low-energy range and emits light. The first photo-detecting section 16 of the first photo-detecting device 14 is fixed to a front side of the first scintillator layer 24 by a first adhesive 25, and converts light emitted by the first scintillator layer 24 to an electrical signal. The first adhesive 25 may be filled not only between the first scintillator layer 24 and the first photo-detecting device 14, but also in the first gap 13, and may not be filled.

The first scintillator layer 24 is integrally formed of, for example, gadolinium, in the longitudinal direction of the slit 7a, in a tape shape with a thickness of approximately 0.1 mm. The width of the first scintillator layer 24, when viewed from the front side, in the direction perpendicular to the predetermined direction, is wider than that of the slit 7a.

On the front side of the second photo-detecting device 21 and the second gap 19, disposed is a second scintillator layer 26 that extends along the predetermined direction, and absorbs X-rays in the high-energy range and emits light. The second photo-detecting section 23 of the second photo-detecting device 21 is fixed to a rear side of the second scintillator layer 26 by a second adhesive 27, and converts light emitted by the second scintillator layer 26 to an electrical signal. The second adhesive 27 may be filled not only between the second scintillator layer 26 and the second photo-detecting device 21, but also in the second gap 19, and may not be filled.

The second scintillator layer 26 has a plurality of scintillator portions 28 disposed one-dimensionally along the predetermined direction, so as to face each of the second photo-detecting sections 23 in the incident direction of X-rays, and a reflection layer 29 that covers the scintillator portion 28 excluding a surface to which the second photo-detecting section 23 facing in the incident direction of X-rays is fixed. The scintillator portion 28, which absorbs X-rays in a high-energy range and emits light, is formed of, for example, cadmium tungstate, in a quadrangular prism shape with a bottom surface of approximately 0.4 mm×0.4 mm and a height of approximately 2 mm, in order to maintain a high resolution while reliably absorbing X-rays in the high-energy range. The reflection layer 29 is formed by adhering to the scintillator portion 28 a light shielding plate evaporated with a metal such as, for example, aluminum, and passes X-rays, and also reflects light emitted by the first scintillator layer 24 and light emitted by the scintillator portion 28. In this case, it is preferable that the other surfaces of the scintillator portion 28 than the surface where the scintillator portion 28 and the second photo-detecting section 23 are fixed are covered with a reflection plate to form the reflection layer 29. In the reflection layer 29, the thickness of parts 29a facing each other in the direction perpendicular to the predetermined direction when viewed from the front side is thicker than that of the other part. The reflection layer 29 may be a reflection film formed by evaporating aluminum on the scintillator portion 28.

Also, with regard to the hardness of the first adhesive 25 used for fixation of the first scintillator layer 24 and the first photodetector 11 and the hardness of the second adhesive 27 used for fixation of the second scintillator layer 26 and the second photodetector 17, the hardness of an adhesive used, of a difference in first temperature deformation amount between the first scintillator layer 24 and the first photodetector 11 and a difference in second temperature deformation amount between the second scintillator layer 26 and the second photodetector 17, for those with a greater difference in temperature deformation amount is lower than that of an adhesive used for those with a smaller difference in temperature deformation amount. In the present embodiment, because a first scintillator material and a second scintillator material are different from each other, the temperature deformation amount is different. Here, as the hardness of an adhesive, for example, a Shore hardness (JIS Z2246) can be applied. Moreover, the first scintillator layer 24 and the second scintillator layer 26 (with the reflection layer 29 provided) are brought in contact with each other so as to slide in contact. Both of an interface between the first scintillator layer 24 and the reflection layer 29 and an interface between the second scintillator layer 26 and the reflection layer 29 may be respectively fixed by an adhesive, or only either one thereof may be fixed by adhesion. In the former case, as in the above, the hardness of an adhesive used, of a difference in first temperature deformation amount between the first scintillator layer 24 and the first photodetector 11 and a difference in second temperature deformation amount between the second scintillator layer 26 and the second photodetector 17, for those with a greater difference in temperature deformation amount is lower than that of an adhesive used for those with a smaller difference in temperature deformation amount. Using an adhesive different in hardness according to the difference in temperature deformation amount allows preventing peeling at an interface between the reflection layer 29 and the scintillator, and peeling at an interface between the detector and scintillator. Moreover, in the latter, because the first scintillator layer 24 and the second scintillator layer 26 are brought in contact with each other so as to slide in contact via the reflection layer 29, peeling at each interface caused by a difference in temperature deformation amount can be prevented. In addition, the configuration of the first scintillator layer 24 is different from that of the second scintillator layer 26, such that the thickness of the first scintillator layer 24 is considerably thinner than that of the second scintillator layer 26.

On the first substrate 12 of the first photodetector 11, an electrical signal outputting connector 31 is connected. An electrical signal output from the first photodetector 11 is transmitted to the computer 54 via the connector 31 and an A/D conversion-scan conversion circuit board 33 or the like. Similarly, on the second substrate 18 of the second photodetector 17, an electrical signal outputting connector 32 is connected. An electrical signal output from the second photodetector 17 is transmitted to the computer 54 via the connector 32 and an A/D conversion-scan conversion circuit board 34 or the like.

Operation of the non-destructive inspection system 50 applied with the X-line sensor 1 configured as above will be described.

X-rays emitted from the X-ray source 52 and transmitted through the specimen S pass through the slit 7a and between the wall portions 8a and 8a, and enter the first scintillator layer 24 through the first photodetector 11. X-rays in the low-energy range of the X-rays having entered the first scintillator layer 24 are absorbed by the first scintillator layer 24, and at this time, light emitted by the first scintillator layer 24 is converted to an electrical signal by the first photo-detecting section 16 of the first photodetector 11. This electrical signal is transmitted to the computer 54 via the amplifier circuit 15 of the first photodetector 11, the connector 31 and the A/D conversion-scan conversion circuit board 33 or the like, and an X-ray transmission image in the low-energy range is obtained by the computer 54.

X-rays in the high-energy range of the X-rays having entered the first scintillator layer 24 are transmitted through the first scintillator layer 24 and the reflection layer 29 and absorbed by the scintillator portion 28 of the second scintillator layer 26, and at this time, light emitted by the scintillator portion 28 is converted to an electrical signal by the second photo-detecting section 23 of the second photodetector 17. This electrical signal is transmitted to the computer 54 via the amplifier circuit 22 of the second photodetector 17, the connector 32 and the A/D conversion-scan conversion circuit board 34 or the like, and an X-ray transmission image in the high-energy range is obtained by the computer 54.

Then, the X-ray transmission image in the low-energy range and the X-ray transmission image in the high-energy range obtained simultaneously are applied with a predetermined processing (for example, a weighted subtraction, superimposition, or the like) by the computer 54, so that a processed image of the specimen S is prepared. This allows realizing, for the specimen S being conveyed by the belt conveyor 51, detection of a foreign substance, measurement of the component distribution, measurement of the weight, and the like at high accuracy.

As described above, in the X-ray line sensor 1, as shown in FIG. 4, the first scintillator layer 24 that absorbs X-rays in the low-energy range and emits light and the second scintillator layer 26 that absorbs X-rays in the high-energy range and emits light are brought in contact with each other, and further, the thickness of the first scintillator layer 24 disposed on the front side is thinner than that of the second scintillator layer 26 disposed on the rear side (is smaller than a center-to-center distance of adjacent first photo-detecting sections 16). These make the amount of mismatch small between a light emitting position P1 in the first scintillator layer 24 and a light emitting position P2 in the second scintillator layer 26 to X-rays in the low-energy range and X-rays in the high-energy range entered at the same angle from the front side, so that at this time, light emitted by the first scintillator layer 24 and light emitted by the second scintillator layer 26 are detected by the first photo-detecting section 16 and the second photo-detecting section 23 facing each other in the incident direction of X-rays. Thus, mismatch between an X-ray transmission image in the low-energy range and an X-ray transmission image in the high-energy range obtained simultaneously can be prevented.

Moreover, in the X-ray line sensor 1, as shown in FIG. 2, one edge portion 12a of the first substrate 12 with the first photo-detecting section 16 provided is located outside further than one edge portion 18a of the second substrate 18 with the second photo-detecting section 23 provided, and conversely, the other edge portion 18b of the second substrate 18 is located outside further than the other edge portion 12b of the first substrate 12. Therefore, even when the first substrate 12 and the second substrate 18 approach each other as a result of reducing the thickness of the first scintillator layer 24, by disposing the amplifier circuit 15, the connector 31, and the like at a part not overlapping the second substrate 18 in the first substrate 12 as well as disposing the amplifier circuit 22, the connector 32, and the like at a part not overlapping the first substrate 12 in the second substrate 18, irradiation of X-rays onto the amplifier circuit 15, 22, the connector 31, 32, and the like can be avoided.

Moreover, in the X-line sensor 1, the slit structure 6 to pass X-rays has the first plate-like member 7 formed with the slit 7a extending in the predetermined direction and the second plate-like member 8 that supports the first plate-like member 7 from the rear side, and in the second plate-like member 8, the wall portion 8a provided in a standing condition toward the rear side is formed along one edge portion and the other edge portion of the slit 7a. Because of this, even when a relatively soft material such as lead is used for the first plate-like member 7 so as to reliably shield X-rays, deformation of the slit 7a formed in the first plate-like member 7 is prevented by the second plate-like member 8, so that X-rays can be made incident reliably on a line along the predetermined direction. Also, the wall portion 8a functions not only as a slit for X-rays but also as a rib to improve bending strength of the second plate-like member 8.

Moreover, in the X-line sensor 1, the width of the first scintillator layer 24 is wider than that of the slit 7a, when viewed from the front side, in the direction perpendicular to the predetermined direction. This, even when the thickness of the first scintillator layer 24 is reduced, allows suppressing a decline in strength of the first scintillator layer 24, as well as making the first scintillator layer 24 reliably absorb X-rays in the low-energy range.

Moreover, in the X-ray line sensor 1, as shown in FIG. 4, the first photo-detecting sections 16, at least two of which being formed on each of the plurality of first photo-detecting devices 14 disposed one-dimensionally along the predetermined direction with the first gap 13 being secured therebetween, are thus disposed one-dimensionally along the predetermined direction, and the first scintillator layer 24 is disposed on the rear side of the first photo-detecting device 14 and the first gap 13. This allows the adjacent photo-detecting devices 14 and 14 to avoid contact and damage with each other, as well as preventing, in the first photodetector 11, a dead zone from being generated on a line along the predetermined direction, because the scintillator layer 24 is disposed not only on the photo-detecting device 14 but also on the gap 13 between the adjacent photo-detecting devices 14.

Similarly, the second photo-detecting sections 23, at least two of which being formed on each of the plurality of second photo-detecting devices 21 disposed one-dimensionally along the predetermined direction with the second gap 19 being secured therebetween, are thus disposed one-dimensionally along the predetermined direction, and the second scintillator layer 26 is disposed on the front side of the second photo-detecting device 21. This allows the adjacent photo-detecting devices 21 and 21 to avoid contact and damage with each other.

Moreover, in the X-ray line sensor 1, the second scintillator layer 26 has the plurality of scintillator portions 28 disposed one-dimensionally along the predetermined direction, and the reflection layer 29 that covers the scintillator portion 28 excluding a surface to which the second photo-detecting section 23 facing in the incident direction of X-rays is fixed. In addition, the scintillator portion 28 absorbs X-rays in the high-energy range and emits light, and the reflection layer 29 passes X-rays, and also reflects light emitted by the first scintillator layer 24 and light emitted by the scintillator portion 28, and as shown in FIGS. 3 and 4, is formed so that the thickness of the parts 29a facing each other in the direction perpendicular to the predetermined direction when viewed from the front side becomes thicker than that of the other part. These allow preventing crosstalk from being generated between the adjacent second photo-detecting sections 23. Further, even when the scintillator portion 28 of the second scintillator layer 26 is in a prism shape in order to maintain a high resolution while reliably absorbing X-rays in the high-energy range, because the reflection layer 29 is formed so that the thickness 29a of the parts facing each other in the direction perpendicular to the predetermined direction becomes thicker than that of the other part, the scintillator portion 28 can be reliably supported. Also, because the thickness of the first scintillator layer 24 is thinner than that of the second scintillator layer 26, even without providing a shielding layer for separating each first photo-detecting section 16 in the first scintillator layer 24, there is almost no influence of crosstalk between the adjacent first photo-detecting sections 16 and 16.

The present invention is by no means limited to the embodiment described above. For example, in the above-mentioned embodiment, the configuration of the first photodetector 11 is substantially identical to that of the second photodetector 17 from the standpoint of lowering the manufacturing cost, however, the configuration of the first photodetector 11 may be different from that of the second photodetector 17.

INDUSTRIAL APPLICABILITY

According to the present invention, it becomes possible to improve reliability of the radiation detector.

The invention claimed is:

1. A radiation detector that detects radiation in a first energy range and radiation in a second energy range entered from a front side, comprising:
   a first scintillator layer extending along a predetermined direction, for converting radiation in the first energy range to light;
   a first photodetector having a plurality of first photo-detecting sections being disposed one-dimensionally along the predetermined direction and fixed to a front side of the first scintillator layer, for converting light converted by the first scintillator layer to an electrical signal, and a first substrate with the first photo-detecting sections provided;
   a second scintillator layer extending in the predetermined direction and being brought in contact with a rear side of the first scintillator layer, for converting radiation in the second energy range to light; and
   a second photodetector having a plurality of second photo-detecting sections being disposed one-dimensionally along the predetermined direction and fixed to a rear side of the second scintillator layer, for converting light converted by the second scintillator layer to an electrical signal, and a second substrate with the second photo-detecting sections provided, wherein
   direction of extension of the first substrate and direction of extension of the second substrate are identical to each other,
   when viewed from a front side, in a direction perpendicular to the predetermined direction, one edge portion of the first substrate is located outside further than one edge portion of the second substrate, and the other edge portion of the second substrate is located outside further than the other edge portion of the first substrate.

2. The radiation detector according to claim 1, comprising a slit structure being disposed on a front side of the first photodetector, for passing radiation in the first energy range and radiation in the second energy range, wherein
   the slit structure has a first plate-like member formed with a slit extending in the predetermined direction, and a second plate-like member that supports the first plate-like member from a rear side, and
   in the second plate-like member, a wall portion provided in a standing condition toward the rear side is formed along one edge portion and the other edge portion of the slit.

3. The radiation detector according to claim 2, wherein when viewed from a front side, in a direction perpendicular to the predetermined direction, the first scintillator layer has a width wider than that of the slit.

4. The radiation detector according to claim 1, wherein the first photo-detecting sections, at least two of which being formed on each of a plurality of first photo-detecting devices disposed one-dimensionally along the predetermined direction with a first gap being secured therebetween, are thus disposed one-dimensionally along the predetermined direction,
   the first scintillator layer is disposed on a rear side of the first photo-detecting device and the first gap,
   the second photo-detecting sections, at least two of which being formed on each of a plurality of second photo-detecting devices disposed one-dimensionally along the predetermined direction with a second gap being secured therebetween, are thus disposed one-dimensionally along the predetermined direction, and
   the second scintillator layer is disposed on a front side of the second photo-detecting device.

5. The radiation detector according to claim 1, wherein
the second scintillator layer has a plurality of scintillator portions disposed one-dimensionally along the predetermined direction, and a reflection layer that covers the scintillator portion excluding a part to which the second photo-detecting section is fixed,
the scintillator portion converts radiation in the second energy range to light, and
the reflection layer passes radiation in the second energy range, and also reflects light converted by the first scintillator layer and light converted by the scintillator portion, and is also formed so that parts facing each other in a direction perpendicular to the predetermined direction when viewed from a front side has a thickness thicker than that of the other part.

6. A radiation detector that detects radiation in a first energy range and radiation in a second energy range entered from a front side, comprising:
   a first scintillator layer extending along a predetermined direction, for converting radiation in the first energy range to light;
   a first photodetector having a plurality of first photo-detecting sections being disposed one-dimensionally along the predetermined direction and fixed to a front side of the first scintillator layer, for converting light converted by the first scintillator layer to an electrical signal, and a first substrate with the first photo-detecting sections provided;
   a second scintillator layer extending in the predetermined direction and being brought in contact with a rear side of the first scintillator layer, for converting radiation in the second energy range to light; and
   a second photodetector having a plurality of second photo-detecting sections being disposed one-dimensionally along the predetermined direction and fixed to a rear side of the second scintillator layer, for converting light converted by the second scintillator layer to an electrical signal, and a second substrate with the second photo-detecting sections provided, wherein
   the first scintillator layer has a thickness thinner than that of the second scintillator layer,
   the second scintillator layer has a plurality of scintillator portions disposed so as to oppose each of the second photo-detecting sections, and a reflection layer provided so as to separate the scintillator portions from one another, and
   the first scintillator layer has a length in a direction perpendicular to the predetermined direction longer than that of the scintillator portions in a direction perpendicular to the predetermined direction.

7. A radiation detector that detects radiation in a first energy range and radiation in a second energy range, comprising:
   a first photodetector having a first scintillator layer extending along a first direction and a first photo-detecting device extending along the first direction, for detecting radiation in the first energy range;
   a second photodetector having a second scintillator layer extending in the first direction and a second photo-detecting device extending along the first direction, for detecting radiation in the second energy range;
   a mechanism having an opening for directing radiation to the first photodetector and to the second photodetector; and
   a slit structure being supported by the mechanism and having a slit portion extending along the first direction, wherein
   the slit structure has a first plate-like member having a slit extending along the first direction and being composed of a material for shielding radiation, and a second plate-like member supporting the first plate-like member and having a wall portion protruding therefrom in a second direction perpendicular to the first direction, and
   the wall portion is disposed inside the opening of the mechanism.

8. The radiation detector according to claim 7, wherein the opening has a length in the second direction longer than that of the wall portion in the second direction.

9. The radiation detector according to claim 7, wherein the wall portion has a first wall portion corresponding to one edge portion of the slit, and a second wall portion corresponding to the other edge portion of the slit.

* * * * *